(12) United States Patent
Davis et al.

(10) Patent No.: US 8,045,161 B2
(45) Date of Patent: Oct. 25, 2011

(54) ROBUST DETERMINATION OF THE ANISOTROPIC POLARIZABILITY OF NANOPARTICLES USING COHERENT CONFOCAL MICROSCOPY

(75) Inventors: Brynmor J. Davis, Champaign, IL (US); Paul Scott Carney, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 360 days.

(21) Appl. No.: 12/405,711

(22) Filed: Mar. 17, 2009

(65) Prior Publication Data

US 2010/0067005 A1  Mar. 18, 2010

Related U.S. Application Data

(60) Provisional application No. 61/037,419, filed on Mar. 18, 2008.

(51) Int. Cl.
*G01N 21/00* (2006.01)

(52) U.S. Cl. .......................... 356/337; 356/336; 356/338

(58) Field of Classification Search .......... 356/335–342, 356/28.5, 301, 427; 250/281, 282, 292, 287–288; 435/6; 977/786, 840
See application file for complete search history.

(56) References Cited

U.S. PATENT DOCUMENTS

| | | | | |
|---|---|---|---|---|
| 4,410,237 A | * | 10/1983 | Veldkamp | 359/572 |
| 5,235,183 A | * | 8/1993 | Whiting et al. | 250/236 |
| 7,119,331 B2 | * | 10/2006 | Chang et al. | 250/292 |
| 7,324,280 B2 | * | 1/2008 | Albert | 359/486.03 |
| 7,372,562 B2 | * | 5/2008 | Islam et al. | 356/301 |
| 7,450,618 B2 | * | 11/2008 | Dantus et al. | 372/25 |
| 7,500,953 B2 | * | 3/2009 | Oraevsky et al. | 600/458 |
| 7,528,959 B2 | * | 5/2009 | Novotny et al. | 356/496 |
| 7,639,359 B2 | * | 12/2009 | Chung et al. | 356/338 |
| 7,876,359 B2 | * | 1/2011 | von Flotow et al. | 348/208.14 |
| 7,876,436 B2 | * | 1/2011 | Chu | 356/338 |
| 2004/0038264 A1 | * | 2/2004 | Souza et al. | 435/6 |

OTHER PUBLICATIONS

Abouraddy et al. "*Three-dimensional Polarization Control in Microscopy*", Physical Review Letters, vol. 96, p. 153901-1-153901-4, 2006.

Beversluis, et al. "*Programmable vector point-spread function engineering*," Optics Express vol. 14, No. 7, pp. 2650-2656, Apr. 3, 2006.

Canfield, et al. "*Chirality arising from small defects in gold nanoparticle arrays*," Optics Express, vol. 14, No. 2, pp. 950-955, Jan. 23, 2006.

Cooper, et al. "*Focusing of pseudorandom polarized beams*," Optics Express, vol. 13, No. 4, pp. 1066-1071 Feb. 21, 2005.

(Continued)

*Primary Examiner* — Sang Nguyen
(74) *Attorney, Agent, or Firm* — Sunstein Kann Murphy & Timbers LLP

(57) ABSTRACT

A coherent confocal microscope for fully characterizing the elastic scattering properties of a nanoparticle as a function of wavelength. Using a high numerical aperture lens, two-dimensional scanning and a simple vector beam shaper, the rank-2 polarizability tensor is estimated from a single confocal image. A computationally efficient data processing method is described and numerical simulations show that this algorithm is robust to noise and uncertainty in the focal plane position. The measurement of the polarizability removes the need for a priori assumptions regarding the nanoparticle shape.

8 Claims, 10 Drawing Sheets

OTHER PUBLICATIONS

Davis, et al. "*Nonparaxial vector-field modeling of topical coherence tomography and interferometric synthetic aperture microscopy*," J. Opt. Soc. Am. A, vol. 24, No. 9, pp. 2527-2542, Sep. 2007.

Davis, et al. "*Spectral self-interference microscopy for low-signal nanoscale axial imaging*," J. Opt. Soc. Am. A. vol. 24, No. 11, pp. 3587-3599, Nov. 2007.

De-Castro, et al. "*Registration of Translated and Rotated Images Using Finite Fourier Transforms*," IEEE Trans. Pattern Analysis and Machine Intelligence, vol. PAMI-9, No. 5, pp. 700-703, Sep. 1987.

Failla, et al. "*Orientational Imaging of Subwavelength Au Particles with Higher Order Laser Modes*," Nano Letters, vol. 6, No. 7, pp. 1374-1378, 2006.

Failla, et al. "*Topology measurements of metal nanoparticles with 1 nm accuracy by Confocal Interference Scattering Microscopy*," Optics Express, vol. 15, vol. 14, pp. 8532-8542, Jul. 9, 2007.

Hassey, et al. "*Probing the Chiroptical Response of a Single Molecule*," Science, vol. 314, No. 5804, pp. 1437-1439, Dec. 1, 2006. (Abstract only).

Kulzer, et al. "*Single-Molecule Optics*," Ann. Rev. Phys. Chem. vol. 55, pp. 585-611, 2004.

Ignatovich, et al. "*Real-time and Background-Free Detection of Nanoscale Particles*," Physical Review Letters, vol. 96, pp. 013901-1-013901-4, Jan. 2006.

Muhlschlegel, et al. "*Resonant Optical Antennas*," Science, vol. 308, pp. 1607-1609, Jun. 10, 2005.

Patra, et al. "*Defocused imaging of quantum-dot angular distribution of radiation*," Appl. Phys. Lett. 87, pp. 101103-1-101103-3, 2005.

Patra, et al. "*Image Analysis of Defocused Single-Molecule Images for Three-Dimensional Molecule Orientation Studies*", J. Phys. Chem. A, vol. 108, No. 33, pp. 6836-6841, 2004.

Richards, et al. "*Electromagnetic diffraction in optical systems: II. Structure of the image field in an aplanatic system*," Proceedings of the Royal Society of London, Series A, vol. 253, No. 1274, pp. 358-379, Dec. 15, 1959.

Sonnichsen, et al. "*Gold Nanorods as Novel Nonbleaching Plasmon-Based Orientation Sensors for Polarized Single-Particle Microscopy*", Nano Letters, vol. 5, No. 2, pp. 301-304, 2005.

Török, et al. "*Electromagnetic diffraction of light focused through a planar interface between materials of mismatched refractive indices: an integral representation*," J. Opt. Soc. Am. A, vol. 12, No. 2, pp. 325-332, Feb. 1995.

van Dijk, et al. "*Absorption and scattering microscopy of single metal nanoparticles*", Phys. Chem. Chem. Phys., vol. 8, pp. 3486-3495, 2006.

\* cited by examiner

ROBUST DETERMINATION OF THE ANISOTROPIC POLARIZABILITY OF NANOPARTICLES USING COHERENT CONFOCAL MICROSCOPY

The present application claims priority from provisional application Ser. No. 61/037,419, filed Mar. 18, 2008, the full disclosure of which is hereby incorporated by reference herein.

This invention was developed with Government support under MURI Grant No. F49620-03-10379, awarded by the US Air Force, and under NSF CAREER Grant No. 0239265, awarded by the National Science Foundation. The Government has certain rights in the invention.

TECHNICAL FIELD OF THE INVENTION

The present invention pertains to optical methods and apparatus for determining polarizability characteristics and locations of nanoparticles with high precision and accuracy.

BACKGROUND OF THE INVENTION

Nanoparticles are currently the subject of intense study as surveyed, for example, in G. Schmid, ed., *Nanoparticles: From Theory to Application* (Wiley, 2004), which is incorporated herein by reference. Applications are as diverse as drug delivery, sensing, bio-imaging and sorbent manufacture. Not least among the interesting properties of nanoparticles are their optical characteristics. The optical attributes of nanoparticles are observed in familiar materials such as opal and stained glass. More recently the optical properties of nanostructures have been exploited in applications such as the construction of metamaterials, discussed by Ziolkowski et al., eds., *Metamaterials: Physics and Engineering Explorations* (Wiley, 2006), and the subwavelength containment of fields using optical antennas, as discussed by Mühlschlegel et al., *Resonant optical antennas, Science*, 308, 1607-1609 (2005). With the increasing use of nanoparticles in optical applications it is desirable to be able to characterize the optical response of a single nanoparticle. This work focuses on the elastic scattering properties, which are determined by a wavelength-dependent linear polarizability tensor for sufficiently small nanoparticles.

The polarizability of a nanoparticle is determined both by the constituent material and by the particle size and shape. For purposes of the present description, unless the particular context requires otherwise, the term "nanoparticle" will refer to a scatterer having point-like characteristics, in that its overall dimensions are smaller than the diffraction limit of any radiation used in its characterization. For a known material and geometry, the polarizability may be determined analytically or by computational methods, however, small deviations from the specified shape may introduce significant optical changes—see Canfield et al., *Chirality arising from small defects in gold nanoparticle arrays, Optics Express* 14, 950-955 (2006) for related measurements from nanoparticle arrays. It is, therefore, highly desirable that a means be provided for actually measuring the polarizability using far-field optical measurements, and that is provided by the current invention, as discussed below.

The measurement scheme of the present invention is based on a coherent confocal microscope. Coherent microscopes use interference with a reference beam to holographically record data and hence acquire information regarding the phase of the measured field. While coherent microscopy predates the invention of the laser, modern bright and broadband sources have made spectrally-sensitive coherent microscopy a practical methodology. This is evidenced by the popularity of techniques such as optical coherence tomography (OCT).

In addition to collecting phase-sensitive data, a coherent microscope has the advantage of high sensitivity when compared to a traditional intensity-based system. As a result, coherent microscopy is suitable for true nanoimaging, as demonstrated by results such as the interferometric detection of single viruses and gold particles as small as 5 nm, as reported by Ignatovich et al., *Real-time and background-free detection of nanoscale particles, Phys. Rev. Lett.*, 96, article no. 013,901 (2006).

In coherent microscopy the optical source is usually split into a reference field and a field that is used to illuminate the sample. The light returned from the sample is combined with the reference field and the interferometric features in the data are used for image formation. To exhibit interference the returned light must be coherent with the reference field and at the same wavelength. This means that potentially useful signals from a nanoparticle, such as Raman-scattered, higher-harmonic and/or fluorescent light, are not detected. As a result, the coherent microscope described here is used to measure only the linear component of the nanoparticle polarizability and the three-dimensional position of the nanoparticle.

Traditional microscopy and spectroscopy usually involve the formation of a scalar image on spatial and/or spectral axes. While this image is immediately useful in many applications, it is possible to design sensing systems that form non-scalar images and/or exploit less obvious relationships between the collected data and the imaged objects. A comprehensive discussion is provided by Barrett et al., *Foundations of Image Science* (Wiley-Interscience, 2003), which is incorporated herein by reference. For example, many modern microscopy and imaging systems collect images as a function of polarization state and/or scattering angle. Additionally, in some applications the object can be represented by a small number of parameters which are estimated from the data with very high precision. In single molecule microscopy, the a priori knowledge that the object can be parameterized by the molecule location allows the molecule to be localized with a precision orders of magnitude better than the diffraction limit.

SUMMARY OF THE INVENTION

In accordance with preferred embodiments of the present invention, methods are provided for measuring the polarizability of the nanoparticle as a function of wavelength. The methods have steps of:
  a. illuminating the nanoparticle with an illuminating electromagnetic wave via a first vector beam shaper;
  b. coherently detecting light scattered by the nanoparticle and propagated through a vector analyzer to generate a detected signal; and
  c. performing an inversion of the detected signal based on a comparison of the detected signal to data predicted from a forward scattering model; and
  d. estimating nanoparticle polarizability based on the inversion.

In accordance with further embodiments of the invention, the aforesaid methods may have a further step of spectrally resolving the detected light. The illuminating radiation may be scanned in a plane transverse to the illumination direction. The vector analyzer may, in some cases, be identical to the vector beam shaper.

In accordance with alternate embodiments of the present invention, there may be a further step that entails varying a physical parameter of an environment in which the nanoparticle is disposed. Moreover, the step of estimating nanoparticle polarizability may include minimizing a cost function based on a norm relating the detected signal to an estimate.

In accordance with another aspect of the present invention, an improvement to an optical coherence microscope is provided for estimating linear polarizability of a particle. The improvement has a vector beam shaper disposed within the illuminating beam.

In accordance with yet another aspect of the present invention, a computer program product is provided for use on a computer system for calculating, with respect to a nanoparticle characterized by a polarizabilty, the polarizability of the nanoparticle as a function of wavelength. The computer program product has a computer usable medium containing computer readable program code that includes:

a. program code for generating a forward scattering model based on forward scattering by a point source;
  b. program code for receiving a signal based on coherent detection of light scattered by the nanoparticle and propogated through a vector analyzer;
  c. program code for performing an inversion of the detected signal based on a comparison of the detected signal to data predicted from a forward scattering model; and
  d. program code for estimating nanoparticle polarizability based on the inversion.

DESCRIPTION OF THE FIGURES

The foregoing features of the invention will be more readily understood by reference to the following detailed description, taken with reference to the accompanying drawings, in which.

DESCRIPTION OF SPECIFIC EMBODIMENTS OF THE INVENTION

Figure 1:
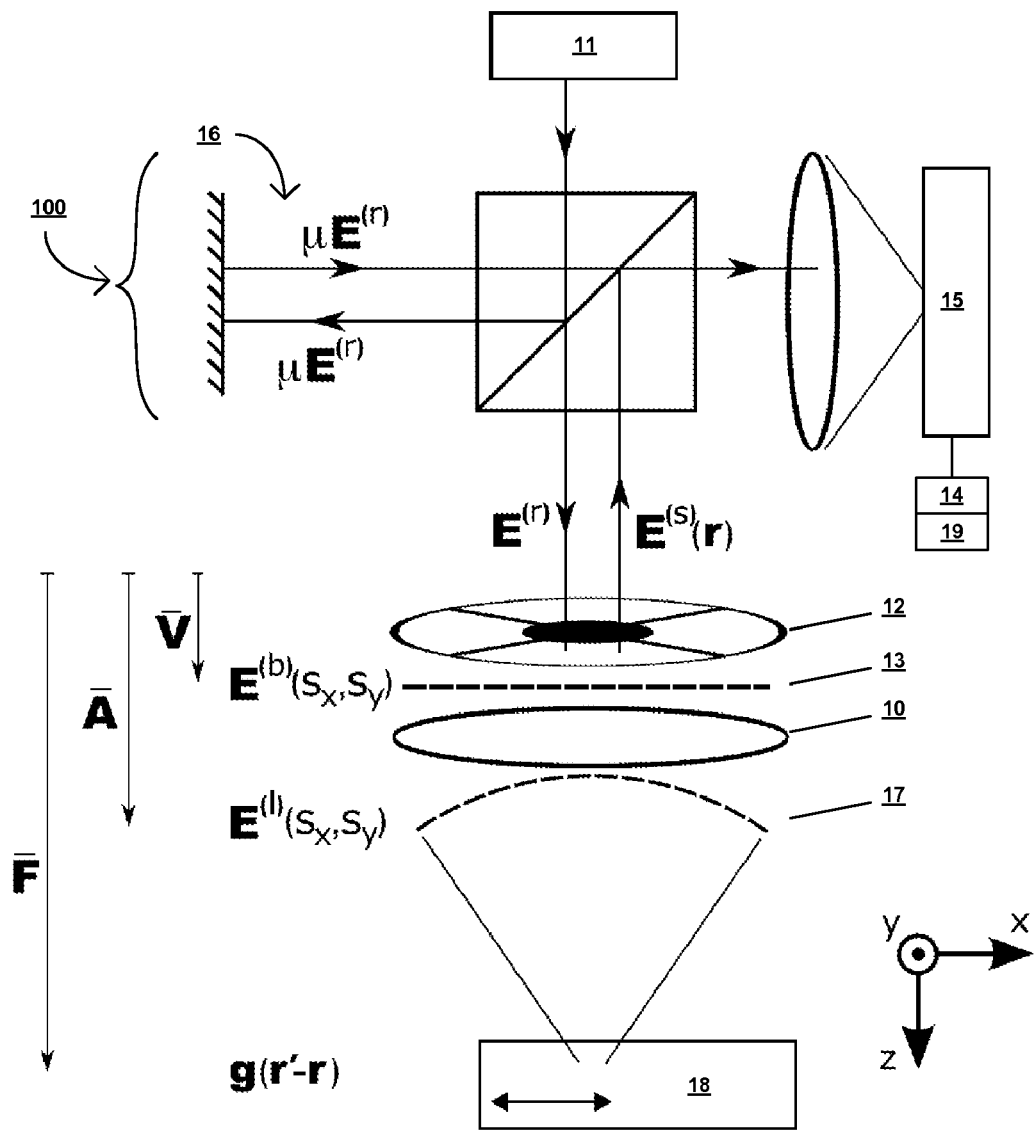
FIG. 1 is a schematic depiction of a coherent confocal system in accordance with preferred embodiments of the present invention, including fields and tensor operators used in the model derivation. The dependence on the wavenumber k has been dropped in the notation and the tensor operators describe the evolution of fields in the direction of the arrows.

Definition. As used in this description and the accompanying claims, the following term shall have the meaning indicated, unless the context otherwise requires:

An "analyzer" is any optical element that breaks the symmetry of an optical system with respect to the vector orientation of an optical field in a plane transverse to its propagation direction. Examples include both static and dynamic polarizers, whether homogeneous or patterned.

In accordance with embodiments of the present invention, a nanoparticle is parameterized by a linear polarizability tensor and a three-dimensional position. This parameterization represents prior knowledge of the object, which is used in conjunction with the instrument sensitivity to the polarization and angular distribution of the scattered light. The nanoparticle parameterization implicitly assumes that the particle is sufficiently small, in relation to the wavelength of light, to be characterized by a point polarizability. However, point-polarizability models may be useful for some larger-particle applications, as well, as they give a coarse first-order description of the scattering for larger particles. In addition, for purposes of the present description, it is assumed that the nanoparticle is sufficiently isolated to preclude interaction with other particles. A mathematical analysis is employed to describe how the particle polarizability affects the data observed in a coherent microscope and shows how the polarizability may subsequently be inferred from the measured data.

The results presented herein build on work from a number of authors. The characteristics of light scattered from a nanoparticle depend on the particle size, shape and orientation—a fact exploited in a number of microscopy modalities, as described by van Dijk et al., *Absorption and scattering microscopy of single metal nanoparticles*, Physical Chemistry Chemical Physics 8, 3486-3495 (2006), which is incorporated herein by reference. The use of the polarization state of light scattered from nanoparticles to identify the two-dimensional orientation of rod-like structures is described by Sönnichsen et al., *Gold nanorods as novel nonbleaching plasmon-based orientation sensors for polarized single-particle microscopy*, Nano Letters 6, pp. 301-4, (2005), which is incorporated herein by reference. Illuminating nanoparticles with a tightly focused vector beam (i.e., a beam with a spatially-varying polarization state) results in incident light with a polarization state dependent on the angle of incidence. A single confocal image formed with the scattered light can then be used to distinguish particle shapes and estimate a two-dimensional orientation angle for rod-like structures, as described by Failla et al., *Orientation imaging of subwavelength Au particles with higher order laser modes*, Nano Letters 6, 1374-1378 (2006). More recently, this technique has been extended to interferometric confocal microscopy by Failla et al., *Topology measurements of metal nanoparticles with 1 nm accuracy by confocal interference scattering microscopy*, Optics Express 15, pp. 8532-42 (2007), to provide an enhancement in sensitivity.

In each of the references discussed in the foregoing paragraph, the measurement systems described are sensitive to a subset of nanoparticle shape features. Given a model of the nanoparticle shape(s), expected data can be calculated, which can then be matched to the observed data to estimate features. For example, given that the sample consists of nanorods oriented perpendicular to the optical axis, the data allow the estimation of the azimuthal orientation angle. Failla (2007) suggested that it may not be necessary to assume that the nanorods are perpendicular to the optical axis—i.e., they conjectured that the polar orientation may also be measured, however, they failed to demonstrate how that might be achieved. The present invention enables, for the first time, the measurement of the orientations of all principal axes of a nanoparticle of dimensions below the diffraction limit, including the polar orientation of the dominant axis.

Rather than assuming nanoparticle shape(s) a priori, it may be assumed, instead, only that the particle is small enough to have its linear scattering characterized by a point polarizability. It is shown that a high numerical-aperture (NA) coherent confocal image formed using vector-beam illumination is sufficient to infer the polarizability up to a complex constant. That is, the linear scattering properties of the nanoparticle are measured without a-priori assumptions regarding particle shape. Particle orientation information can be obtained by examining the principal axes of the polarizability tensor. In addition, the system in accordance with the present invention is robust to defocus. Moreover, the data processing algorithms described are computationally inexpensive, although the use of other data processing algorithms is encompassed within the scope of the present invention.

As mentioned above, the principal axes of the polarizability can be related to the orientation of an asymmetric nanoparticle. The orientation of nanoparticles has been determined optically using both scattering and fluorescence measurements. Kulzer et al., *Single-molecule optics*, Annual Rev. Phys. Chem., 55, pp. 585-611 (2004) contrasts the fluorescence signal from a nanoparticle or single molecule with the comparable scattering signal, which is weaker and thus more difficult to detect. Fluorescence-based orientation imaging systems provide a point of comparison for the scattering-based instrument described here. Like the scattering-based systems, fluorescence orientation imaging involves postulating a model describing the relevant nanoparticle optics and estimating the parameters of this model from observed data.

The power coupled into a fluorophore, and hence the fluorescence emission rate, is dependent on the orientation of the fluorophore and the direction of the exciting field. This measurable dependence has resulted in the development of a number of systems where the polarization state of the focused excited field can be controlled. By varying either the exciting polarization state or the detected polarization direction, it has been shown that the orientation of the fluorophore can be determined. Alternatively, it is possible to find the fluorophore orientation by matching observations from high-angle excitation, vector-beam excitation or defocused data to those predicted for different orientations. Most fluorescence orientation imaging systems assume a dipole model for the fluorophore, although chirality has been measured by Hassey et al., *Probing the chiroptical response of a single molecule*, Science 314, pp. 1437-39 (2006), and non-dipolar emission has been measured by Patra et al., *Defocused imaging of quatum-dot angular distribution of radiation*, Appl. Phys. Lett. 87, article no. 101103 (2005).

While scattering is a coherent field-based phenomenon, fluorescence is an incoherent intensity-based effect. For a point-like nanoparticle, scattering is defined by a rank-2 tensor relating the incident field to the scattered field, whereas fluorescence is captured by a rank-4 tensor relating the incident intensity and polarization state to the emitted intensity and polarization state. This rank-4 tensor can be related to optical intensity measurements, as in the model derived by Davis et al., *Spectral self-interference microscopy for low-signal nanoscale axial imaging*, J. Opt. Soc. Am. A 24, pp. 3587-99 (2007), which is incorporated herein by reference. However, due to high dimensionality, this tensor would be difficult to estimate. The assumption of a dipolar fluorophore simplifies the fluorescence tensor and makes fluorophore orientation characterization feasible. In this work we show that such simplifications are not necessary when estimating the rank-2 polarizability tensor that characterizes the linear nanoparticle scattering—the polarizability tensor can be fully estimated from a single coherent confocal image.

In the following section the forward model for the coherent confocal microscope is derived. In the section entitled Approximate Forward Model below, this model is approximated in a manner that reduces the computational cost of the polarizability estimation. The procedure for estimating the polarizability is given in the section entitled Inverse Problem, i.e., the inverse problem is solved. The method is demonstrated and characterized using numerical experiments.

Forward Model

The nanoparticle position and polarizability are determined by selecting values that best explain the measured data. In order to do this, the instrument must be thoroughly modeled. This section describes such a model, which may be generated in process 21 of FIG. 2, following the coherent microscope treatment presented in Davis et al., *Nonparaxial vector-field modeling of optical coherence tomography and interferometric synthetic aperture microscopy*, J. Opt. Soc. Am. 24, pp. 2527-42 (2007), which is incorporated herein by reference and referred to hereinafter as "Davis 2007."

Figure 2:
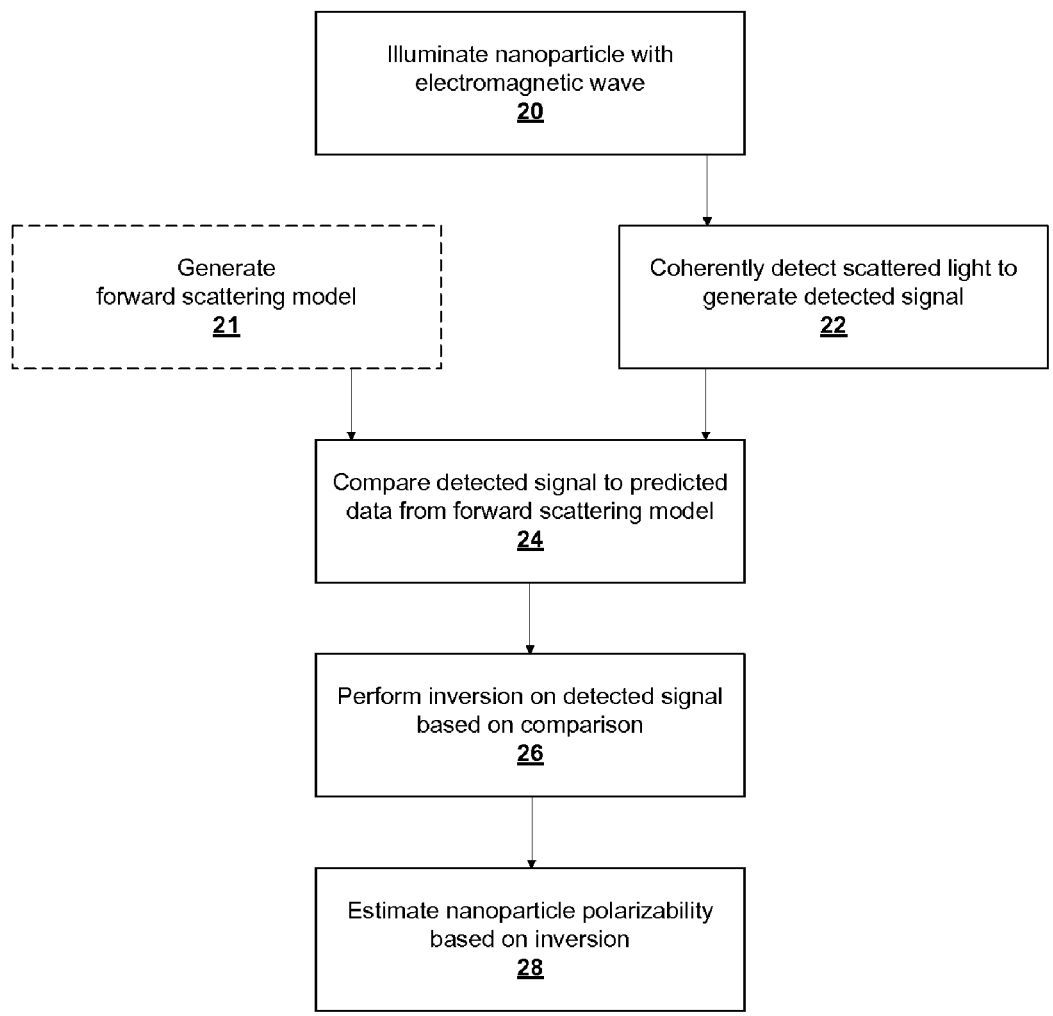
FIG. 2 is a flow chart of a method for measuring polarizability of a nanoarticle as a function of wavelength using the coherent confocal system of FIG. 1 in accordance with an embodiment of the present invention.

With reference to the basic system diagram of FIG. 1 and the process flow diagram of FIG. 2, in process 20 of FIG. 2 a polychromatic reference field $E^{(r)}(k)$ (where k is the wavenumber) is emitted by a source 11 and focused into the object 18 using a lens 10 of high numerical aperture (NA) and a vector-beam shaper 12. The scattered field returned from the sample 18 is denoted by $E^{(s)}(r; k)$, where r gives the geometrical focus of the lens 10. In process 22 of FIG. 2 the scattered field is combined with the reference field by an interferometer, designated generally by numeral 100, which collects the combined fields at a spectrometer 15, and the collected field is averaged at a detector 14 connected to the spectrometer 15.

Data from the detector is processed by a processor 19 according to the techniques described in detail below. In some embodiments, the processor may perform control functions, such as directing the physical displacement of sample 18 during scanning. The data collected are thus proportional to the total spectral density $$I(r; k) = \langle |\mu E^{(r)}(k) + E^{(s)}(r; k)|^2 \rangle, \quad (1)$$
$$= \langle |\mu E^{(r)}(k)|^2 \rangle + 2\text{Re}\{S(r; k)\} + \langle |E^{(s)}(r; k)|^2 \rangle,$$

where μ is a constant that accounts for any depletion of the reference field and ⟨ · ⟩ indicates an expected value. The interferometric cross term is $$S(r;k) = \langle [\mu E^{(r)}(k)]^\dagger E^{(s)}(r;k) \rangle, \quad (2)$$

where † is the Hermitian transpose operator.

The first term in Eqn. (1) is constant with r and can be removed. The third (autocorrelation) term is typically of much lower magnitude than the other two terms and will be assumed negligible. Finally, by setting the path length of the interferometer reference arm 16 to be shorter than the minimum path to the sample 18, the complex signal S can be recovered from the measured real part using Hilbert transform processing, as discussed in Davis 2007.

As seen in FIG. 1, the plane-wave reference field $E^{(r)}$ falling on the vector-beam shaper 12 produces a field $E^{(b)}$ on the entrance pupil 13 of the objective lens 10, and this field in turn maps to field $E^{(l)}$ on the exit pupil 17 of the lens 10. Following standard practice, the vector-beam shaper 12 and the objective lens 10 will be modeled using geometrical optics. The variables $s_x$ and $s_y$ refer to the x and y components of a unit vector directed from a point on the exit pupil 17 toward the geometrical focus. Each such ray can be traced back to a point on the entrance pupil 13. In this case an infinity-corrected aplanatic lens is assumed so each (z-directed) ray passing through the beam shaper 12 to the entrance pupil 13 emerges at the same (x,y) location on the exit pupil 17.

The field $E^{(b)}$ is determined by the illuminating reference field and a tensor operator $\overline{\nabla}$ representing the action of the beam shaper 12, i.e., $$E^{(b)}(s_x, s_y; k) = \overline{\nabla}(s_x, s_y) E^{(r)}(k). \quad (3)$$

Here represents a tensor and, for simplicity, the beam shaper is assumed to be independent of k. It is to be understood that any implementation of a beam shaper is within the scope of the present invention. In particular, in one embodiment, the beam shaper may be a spatially-uniform polarization analyzer, rotated between sequential measurements.

Figure 3:
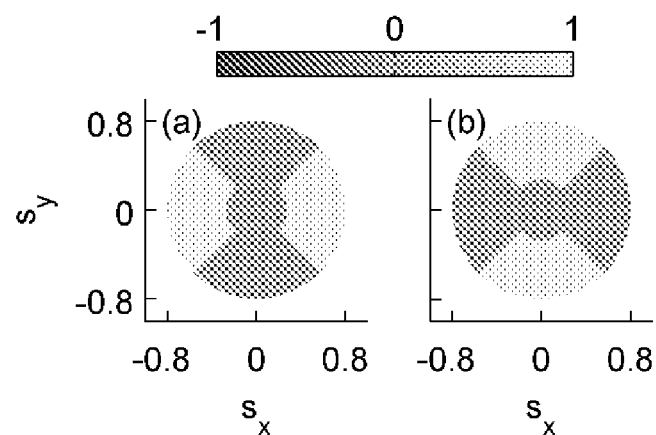
FIG. 3 depicts the optical field at entrance pupil, $E^{(b)}$. The field direction is parallel to the entrance pupil with the x-directed (a) and y-directed (b) fields shown separately. The field is displayed as a function of the cosines of the angles to focus over the 0.8-NA lens aperture.

The vector-beam shaper 12 is used to produce diversity in the polarization states at the entrance pupil 13. In this case the beam shaper is partitioned into quadrants and half-wave plates employed to rotate the polarization state of the incident field. As illustrated in FIG. 3, two quadrants are x-polarized and two components are y-polarized. The center of the beam shaper is opaque and the action of the beam shaper is assumed to produce negligible deviation from the z-directed propagation of the incident field.

The mapping from $E^{(b)}$ to $E^{(l)}$ is given by a standard tensor operator, obtained from simple rotations of Eq. (2.23) in Richards et al., *Electromagnetic diffraction in optical systems. II. Structure of the image field in an aplanatic system*, Proc. Royal Soc. London. Series A, 253, pp. 359-79 (1959), hereinafter Richards (1959), which is incorporated herein by reference in its entirety. The tensor operator $\overline{A}$ contains this operation and the action of the beam shaper so that the field at the lens exit pupil is $$E^{(l)}(s_x, s_y; k) = \overline{A}(s_x, s_y) E^{(r)}(k). \quad (4)$$

Figure 4:
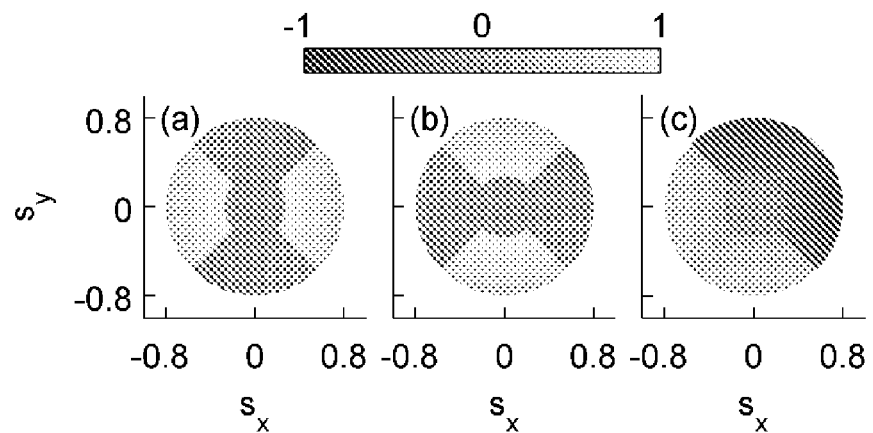
FIG. 4 depicts the optical field at exit pupil, $E^{(f)}$. The x-directed (a), y-directed (b) and z-directed (c) fields are shown separately. The field is displayed as a function of the cosines of the angles to focus over the 0.8-NA lens aperture.

The field $E^{(l)}$ for the example system is shown in FIG. 4. It can be seen that the high NA (0.8) produces high angles-to-focus and hence significant z components in the electric field. Blocking the center of the beam-shaper ensures that these z-directed components are of a similar magnitude to the x and y components. It will be seen that the diversity of polarization states at the exit pupil is critical in the estimation of the nanoparticle polarizability.

Each position on the exit pupil is associated with an angle-to-focus. This means that the field $E^{(l)}$ can be regarded as an angular spectrum which can then be used to calculate the focused field in the object. For a position r' in the object and a geometrical focus r, the focused field is $$g(r' - r; k) = \frac{k}{2\pi i} \int_\Omega ds_x ds_y \frac{\overline{A}(s_x, s_y) E^{(r)}(k)}{s_z(s_x, s_y)} e^{iks \cdot (r' - r)}, \quad (5)$$
$$= \overline{F}(r' - r; k) E^{(r)}(k),$$

where $$s_z(s_x, s_y) = \sqrt{1 - s_x^2 - s_y^2}, \quad (6)$$

$s = (s_x, s_y, s_z)^T$ (T is the transpose operator) and integration is over the unit disk $\Omega = \{s_x, s_y: s_x^2 + s_y^2 < 1\}$. Use of this angular spectrum framework to describe focusing into a sample with a background-index mismatch was described by Török et al., *Electromagnetic diffraction of light focused through a planar interface between materials of mismatched refractive indices: an integral representation*, J. Opt. Soc. Am. A 12, pp. 325-32 (1995).

Figure 5:
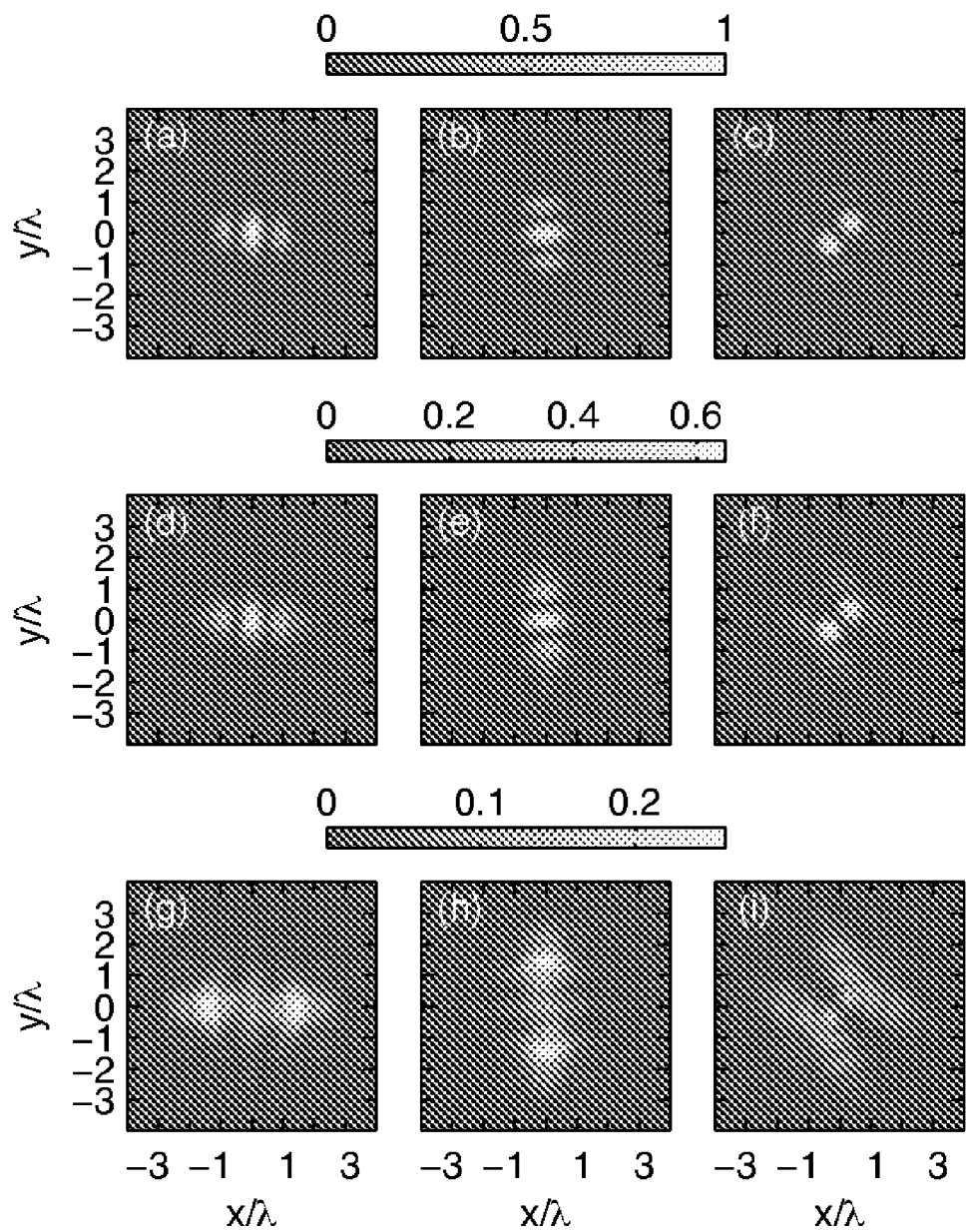
FIG. 5 shows calculated intensities of the focused field g(x, y, z; k) at z=0 (a-c), z=λ(d-f) and z=2λ(g-i), where the wavelength is given by $\lambda=2\pi/k$. The intensities of each component are plotted separately—i.e., $|g_x|^2$ (a,d,g), $|g_y|^2$ (b,e,h) and $|g_z|^2$ (c,f,i) are shown on different plots.

The exit pupil fields from FIG. 4 produce the focused intensities seen in FIG. 5. The beam focusing described here is similar to a pseudo-radial beam described by Cooper et al., *Focusing of pseudorandom polarized beams*, Optics Express 13, pp. 1066-71 (2005) except that opposing quadrants in FIG. 3 do not have opposing signs. Field engineering approaches such as pseudo-radial beams and such as those mentioned in Beversluis et al., *Programmable vector point-spread function engineering*, Optics Express 14, pp. 2650-56 (2006) provide physical manipulation of a vector beam to produce a desired polarization state at focus. Within the scope of the present invention, it is required only that the focal field consists of a spectrum of components with diverse polarization states—the value of the resulting field at focus is not important. For example, in FIG. 5 it can be seen that the field at the geometrical focus has no z component, while a focused pseudo-radial beam produces a purely z-oriented field. Both a pseudo-radial system or the example described here will allow determination of the nanoparticle polarizability.

The illuminating field interacts with a nanoparticle at position $r^{(p)}$ with polarizability $\overline{\alpha}(k)$. This produces a scattering source $k^2 \overline{\alpha}(k) g(r^{(p)} - r; k)$. This scattered light propagates back through the system to produce the—z-propagating field $E^{(s)}$. The scattered light passes through a vector analyzer, which, for simplicity of description is assumed to be identical to the vector shaper in the illuminating beam, although that is not required within the scope of the present invention as claimed. Assuming, for convenience of description, that the lens and beam shaper obey reciprocity, the tensor operator $\overline{F}^T$ describes propagation back through the system so that $$E^{(s)}(r;k) = k^2 \overline{F}^T(r^{(p)} - r;k) \overline{\alpha}(k) g(r^{(p)} - r;k). \quad (7)$$

The complex data can then be calculated by evaluating Eqn. (2) so that $$S(r;k) = \mu^* k^2 \times \langle [E^{(r)}(k)]^\dagger \overline{F}^T(r^{(p)} - r; k)\overline{\alpha}(k)\overline{F}(r^{(p)} - r; k)E^{(r)}(k)\rangle. \tag{8}$$

Due to the confocal nature of the system, the collected data is second-order in the focused field.

The focal point is scanned over two dimensions $\rho$, where $\rho=(x,y)^T$ and the focal plane is set to lie at $z=0$. Additionally, it will be assumed that unmodeled instrument losses and uncertainties in the path lengths preclude precise knowledge of the absolute scale of the data. As a result, the data can be written, $$S(\rho;k) \propto \alpha_{\zeta\beta}(k) h_{\zeta\beta}(\rho-\rho^{(p)}; z^{(p)}, k), \tag{9}$$

where $$h_{\zeta\beta}(\rho; z^{(p)}, k) = k^2 W_{\kappa\gamma}(k) F_{\beta\gamma}(-\rho, z^{(p)}; k) F_{\zeta\kappa}(-\rho, z^{(p)}; k), \tag{10}$$

with the coherency matrix $$W(k) = \langle E^{(r)}(k)[E^{(r)}(k)]^\dagger \rangle \tag{11}$$

defining the reference polarization state. Einstein summation is applied in Eqns. (9) and (10) over repeated subscripts. From Eqn. (9) it can be seen each component of the polarizability (indexed by $\zeta$ and $\beta$) contributes a point spread function (PSF) term to the data. These PSFs vary with $z^{(p)}$, the defocus of the nanoparticle.

Assuming an adequate sampling rate in $\rho$, a sufficiently small sampling range to isolate a single nanoparticle and a sufficiently large sampling range to collect all of the relevant signal, Eqn. (9) can be rewritten in the Fourier domain as $$\tilde{S}(q;k) \propto \alpha_{\zeta\beta}(k) \tilde{h}_{\zeta\beta}(q; z^{(p)}, k) e^{-iq \cdot \rho^{(p)}}, \tag{12}$$

where ~ denotes a lateral Fourier transform.

The nanoparticle polarizability can be estimated by optimally decomposing the data into a weighted sum of $h_{\zeta\beta}$ or $\tilde{h}_{\zeta\beta}$ terms, where the weights give the elements of the polarizability. The coherent nature of the measurement means that the data are linear in the polarizability elements, which makes them easier to estimate than parameters such as orientation angles, which are nonlinear parameters of the data. Orientation parameters are estimated by nonlinear algorithms such as pattern matching, as described, for example, by Patra et al., *Image analysis of defocused single-molecule images for three-dimensional molecule orientation studies, J. Phys. Chem. A*, 108, pp. 6836-41, (2004). It will be seen that the linear formulation of Eqn. (12) allows efficient estimation of the polarizability.

In order to estimate the polarizability elements $\alpha_{\zeta\beta}$, it is desirable to have a PSF h that varies significantly with $\zeta$ and $\beta$. It can be seen from Eqn. (10) that the PSFs are invariant to a reordering of $\zeta$ and $\beta$. This does not cause a problem, as the polarizability can be seen to be transpose-symmetric by conservation of energy arguments, so that $\alpha_{\zeta\beta} = \alpha_{\beta\zeta}$. That is, the instrument produces six independent PSFs and the polarizability is defined by six independent elements.

The more different the PSFs are, the more recognizable the signature of each polarizability component is in the data. The high-NA lens and vector beam shaper are chosen to give this PSF diversity. The Fourier domain will be used to process the data and examine the PSFs because, as shown in the next section, a Fourier domain representation allows a simplifying approximation. The Fourier-domain representations of the PSFs can be calculated as follows.

The lateral Fourier transform of the illuminating field at a given x-y plane and wavenumber can be found from the representation of Eqn. (5). Specifically, $$\tilde{F}_{\beta\gamma}(q; z, k) = \frac{2\pi}{ik} \frac{A_{\beta\gamma}(q/k)}{s_z(q/k)} e^{iks_z(q/k)z}, \tag{13}$$

expresses the Fourier optics relation between the focused field and the field emerging from the lens. The PSFs are the weighted sum of products of $F_{\beta\gamma}$ components [Eqn. (10)], and in the Fourier domain these products become convolutions so that $$\tilde{h}_{\zeta\beta}(-q; z^{(p)}, k) = -4\pi^2 W_{\kappa\gamma}(k) \tag{14}$$

$$\int_{\mathbb{R}^2} d^2 q' \frac{A_{\beta\gamma}\left(\frac{q-q'}{k}\right) A_{\zeta\kappa}\left(\frac{q'}{k}\right)}{s_z\left(\frac{q-q'}{k}\right) s_z\left(\frac{q'}{k}\right)} \times \exp\left\{ik \left[s_z\left(\frac{q-q'}{k}\right) + s_z\left(\frac{q'}{k}\right)\right] z^{(p)}\right\}.$$

Figure 6:
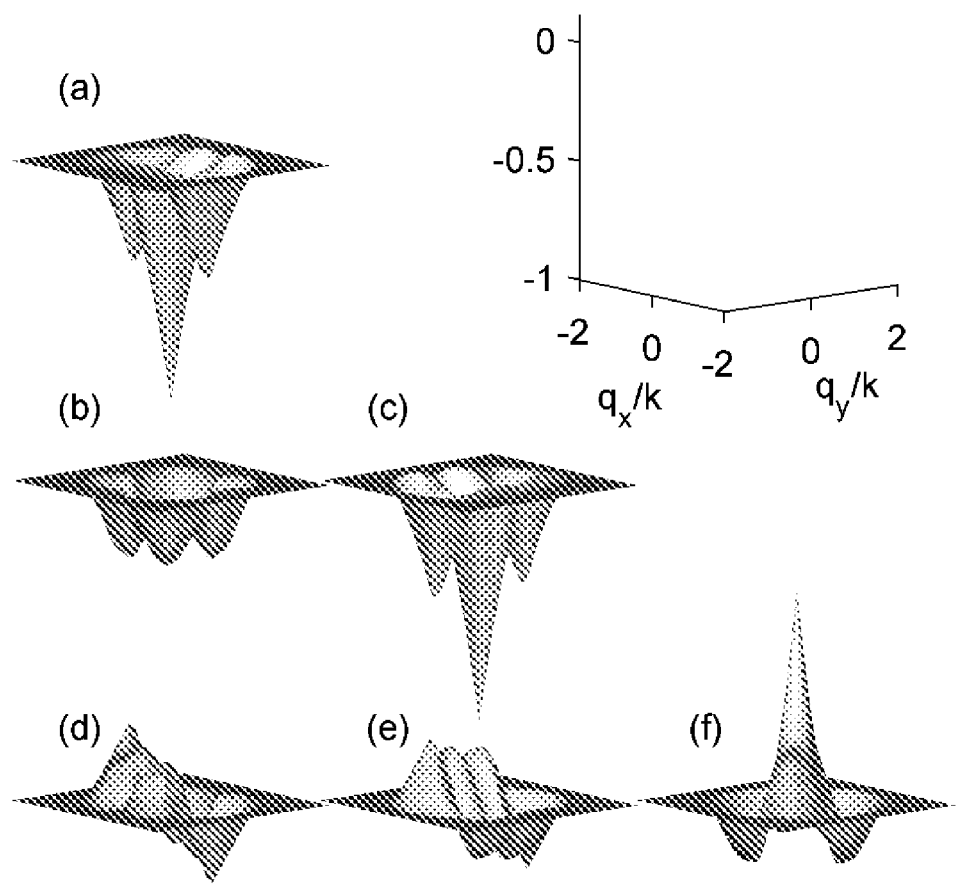
FIGS. 6(a)-(f) are Fourier-domain representations of the focal plane PSFs for the example system. At $z^{(p)}=0$ and for this system, these functions are real fields. The function axes are shown in the upper right and the remaining plots show $\tilde{h}_{xx}$ (a), $\tilde{h}_{xy}$ (b), $\tilde{h}_{yy}$ (c), $\tilde{h}_{xz}$ (d), $\tilde{h}_{yz}$ (e) and $\tilde{h}_{zz}$ (f).

These expressions were evaluated for an exemplary system on the focal plane ($z^{(p)}=0$) and the resulting Fourier spectra are shown in FIG. 6. The exit pupil fields of FIG. 4 can be related to these plots using Eqns. (13) and (14).

Approximate Forward Model

The data expected from a given nanoparticle are described by Eqn. (12), where the PSFs can be calculated using Eqn. (14). The PSFs depend on k via simple axes scaling but depend on the nanoparticle defocus $z^{(p)}$ in a more complicated fashion. As will be seen in the next section, it is necessary to calculate the PSFs repeatedly, at different values of $z^{(p)}$ in order to estimate the nanoparticle polarizability. For this reason, Eqn. (14) will be approximated in a manner that makes numerical evaluation inexpensive in terms of both computations and memory requirements.

Due to the finite extent of $\overline{A}$, the integrand of Eqn. (14) is nonzero only on a circle with a radius of twice the NA. Within this area the magnitude of the integrand is peaked at N points $q' = p(q; \zeta, \beta, n)$, where $n=1, \ldots, N$. The region of integration will be divided into N regions $R(q; \zeta, \beta, n)$, based on these peaks. For low $kz^{(p)}$ the exponential factor in Eqn. (14) is approximated as constant in each region $R(q; \zeta, \beta, n)$, resulting in $$\tilde{h}_{\zeta\beta}(-q; z^{(p)}, k) \approx \tag{15}$$

$$-4\pi^2 \sum_{n=1}^{N} \exp\left\{iks_z\left(\frac{p(q; \zeta, \beta, n)}{k}\right) z^{(p)}\right\} \times \exp\left\{iks_z\left(\frac{q - p(q; \zeta, \beta, n)}{k}\right)\right.$$

$$\left. z^{(p)}\right\} \times W_{\kappa\gamma}(k) \int_{R(q;\zeta,\beta,n)} d^2 q' \frac{A_{\beta\gamma}\left(\frac{q-q'}{k}\right) A_{\zeta\kappa}\left(\frac{q'}{k}\right)}{s_z\left(\frac{q-q'}{k}\right) s_z\left(\frac{q'}{k}\right)}.$$

As shown by Eqns. (13) and (14), the integral under consideration depends on the overlap between offset copies of the patterns shown in FIG. 4. For this example it can be seen that the integrand will generally have one dominant peak at $p(q; \zeta, \beta, 1)$ or, when $\zeta = \beta$, two equally dominant peaks where $p(q; \zeta, \beta, 2) = q - p(q; \zeta, \beta, 1)$. In either of these cases, Eqn. (15) reduces to $$\tilde{h}_{\zeta\beta}(-q; z^{(p)}, k) \approx -4\pi^2 \exp \quad (16)$$

$$\left\{ iks_z\left(\frac{p(q;\zeta,\beta,1)}{k}\right)z^{(p)}\right\} \times \exp\left\{iks_z\left(\frac{q-p(q;\zeta,\beta,1)}{k}\right)z^{(p)}\right\} \times$$

$$W_{\kappa\gamma}(k) \int_{\mathbb{R}^2} d^2q' \frac{A_{\beta\gamma}\left(\frac{q-q'}{k}\right)A_{\zeta\kappa}\left(\frac{q'}{k}\right)}{s_z\left(\frac{q-q'}{k}\right)s_z\left(\frac{q'}{k}\right)},$$

where in the two peak case the fact that the exponential prefactors are equal for p(q; ζ, β, 1) and p(q; ζ, β, 2) has been exploited. This equation can be written in the simple form $$\tilde{h}_{\zeta\beta}(-q;z^{(p)},k) \approx H(q;\zeta,\beta,k)e^{ik\Phi(q;\zeta,\beta,k)z^{(p)}}, \quad (17)$$

where the Fourier transforms of the PSFs for an in-focus particle ($z^{(p)}=0$) are $$H(q;\zeta,\beta,k) = -4\pi^2 W_{\kappa\gamma}(k) \int_{\mathbb{R}^2} d^2q' \frac{A_{\beta\gamma}\left(\frac{q-q'}{k}\right)A_{\zeta\kappa}\left(\frac{q'}{k}\right)}{s_z\left(\frac{q-q'}{k}\right)s_z\left(\frac{q'}{k}\right)}, \quad (18)$$

and defocus contributes a phase term of the form $$\Phi(q;\zeta,\beta,k) = s_z\left(\frac{q-p(q;\zeta,\beta,1)}{k}\right) + s_z\left(\frac{p(q;\zeta,\beta,1)}{k}\right). \quad (19)$$

The approximation represented by Eqn. (17) allows an easy calculation of the system PSFs as a function of the nanoparticle defocus $z^{(p)}$. Within the bounds of this approximation, it is possible to calculate the PSFs at any plane using simple manipulations of H and Φ. These functions vary trivially with k, so it is only necessary to store twelve two-dimensional images (i.e., functions of q) in order to calculate the six PSFs required to characterize the system.

Figure 7:
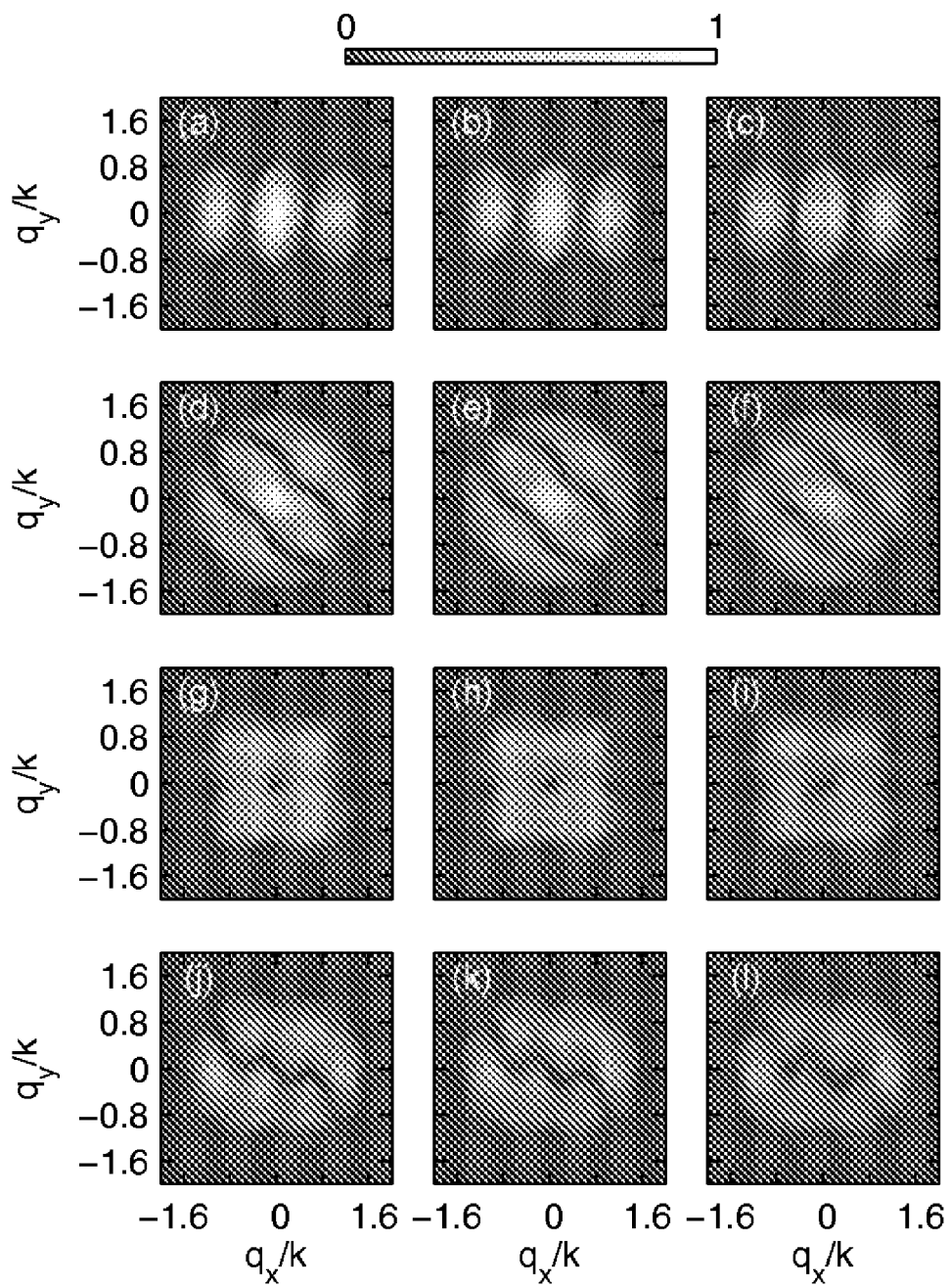
FIG. 7 shows Fourier-domain magnitudes of the system PSFs at $z^{(p)}=0$ (a, d, g, j), $z^{(p)}=\lambda/2$ (b, e, h, k) and $z^{(p)}=\lambda$(c, f, i, l). Magnitudes for $\tilde{h}_{xx}$ (a-c), $\tilde{h}_{zz}$ (d-f), $\tilde{h}_{xy}$ (g-i) and $\tilde{h}_{xz}$ (j-l) are shown with $\tilde{h}_{yy}$ being a rotation of $\tilde{h}_{xx}$ and $\tilde{h}_{yz}$ being a rotation of $\tilde{h}_{xz}$. The first column represents the magnitudes of the plots shown in FIG. 5.
Figure 8:
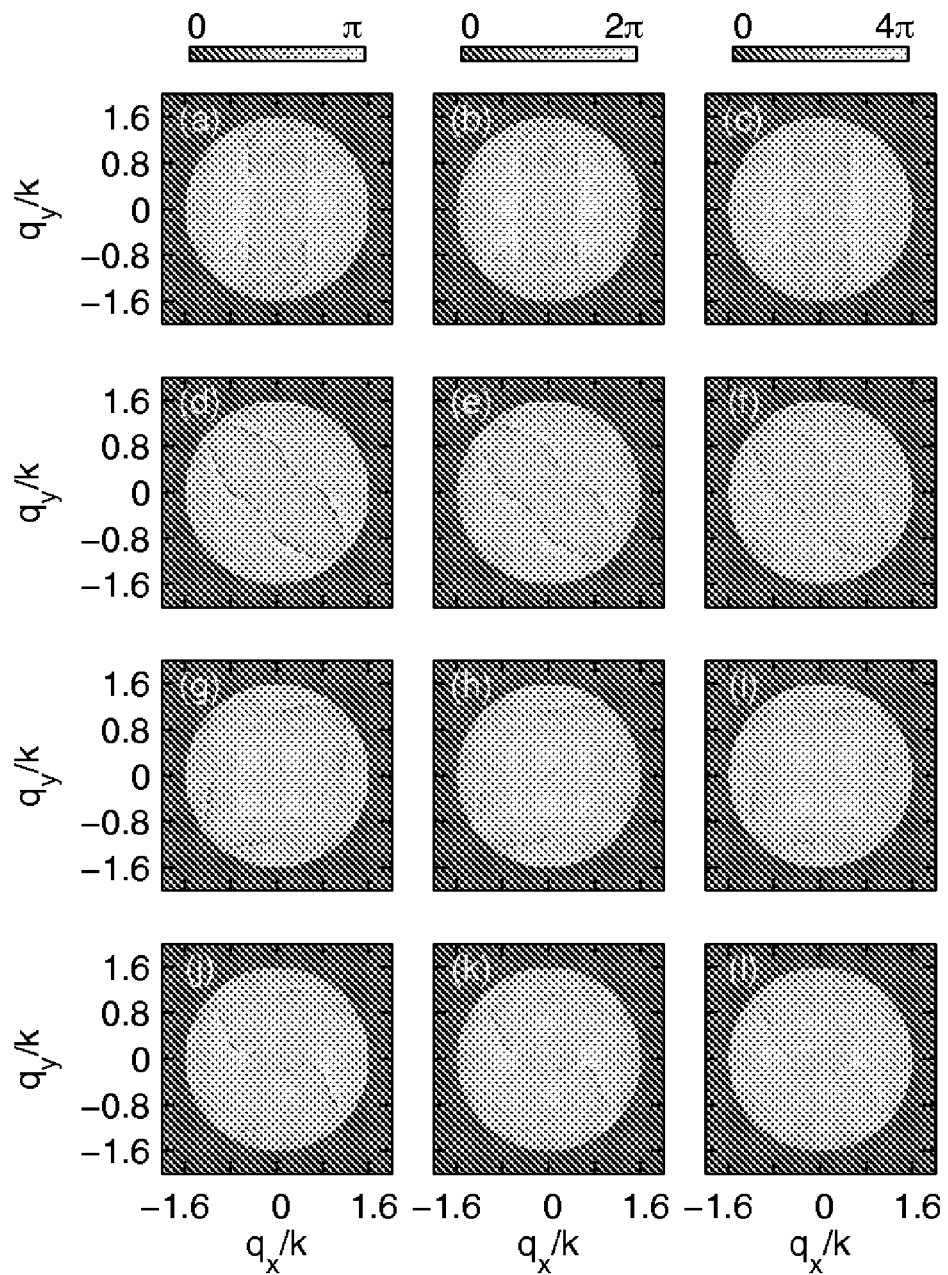
FIG. 8 shows Fourier-domain phase profiles of the system PSFs at $z^{(p)}=\lambda/4$ (a, d, g, j), $z^{(p)}=\lambda/2$ (b, e, h, k) and $z^{(p)}=\lambda$(c, f, i, l). These are calculated by dividing $\tilde{h}$ at $z^{(p)}$ into $\tilde{h}$ at $z^{(p)}=0$ and taking the complex angle. Phases for $\tilde{h}_{xx}$ (a-c), $\tilde{h}_{zz}$ (d-f), $\tilde{h}_{xy}$ (g-i) and $\tilde{h}_{xz}$ (j-l) are shown with $\tilde{h}_{yy}$ being a rotation of $\tilde{h}_{xx}$ and $\tilde{h}_{yz}$ being a rotation of $\tilde{h}_{xz}$. The phase profiles have been unwrapped.

The approximation described in this section can be tested by evaluating Eqn. (14) and examining the behavior of the magnitude and phase across multiple values of $z^{(p)}$. According to Eqn. (17) the resulting magnitude should not change with $z^{(p)}$. The magnitudes calculated for this example are shown in FIG. 7 and it can be seen they are relatively stable with up to a wavelength of defocus. The corresponding phase profiles are shown in FIG. 8, although it should be noted that the $z^{(p)}=0$ column of FIG. 7 has been replaced with $z^{(p)}=\lambda/4$, since the in-focus spectra are real and therefore have no useful phase profile. The images in FIG. 8 are plotted on a scale proportional to $z^{(p)}$, so that the along-row consistency corresponds to a phase profile scaling with $z^{(p)}$, as required by Eqn. (17). Taken together, FIGS. 7 and 8 indicate that the approximation derived in this section is relatively accurate, up to at least a wavelength of defocus.

Inverse Problem

With a forward model formulated, the inverse problem can be addressed. That is, estimating the nanoparticle parameters from the collected data. The inverse problem can be solved by comparing, in process 24 of FIG. 2, the observed data to data predicted using the forward model and a given set of nanoparticle parameters. The set of parameters giving the minimum discrepancy will be chosen as estimated particle characteristics. Mathematically, a cost function can be defined as $$C[\overline{\alpha}(k), r^{(p)}; k] = \left\| \tilde{S}(q;k) - \alpha_{\zeta\beta}(k)\tilde{h}_{\zeta\beta}(q;z^{(p)},k)e^{-iq\cdot\rho^{(p)}} \right\|^2, \quad (20)$$

and minimized with respect to $r^{(p)}$ and $\overline{\alpha}(k)$ at each k value. A Euclidean (i.e., $\ell^2$) norm $\|\cdot\|$ is chosen in Eqn. (20), which is consistent with a Gaussian noise model and maximum likelihood parameter estimation. Moreover, this noise model is consistent with interferometer measurements dominated by noise from the reference beam and/or thermal detector noise.

The Fourier-domain PSFs $\tilde{h}$ used in Eqn. (20) can be calculated using either the unapproximated Eqn. (14) or the approximate Eqn. (17). The approximated calculation is more efficient and involves the precalculation of H and Φ. To find H, Eqn. (18) can be numerically evaluated. Rather than finding Φ by direct evaluation of Eqn. (19) (which involves defining many peaks p), a simpler approach is to evaluate the exact Fourier spectra (using Eqn. (14)) for a small value of $z^{(p)}$, divide by the spectra H, take the complex angle of the result and divide that by $kz^{(p)}$. This algorithm can be justified by examining the form of Eqn. (17).

Regardless of how the PSFs are calculated, the forward model (Eqn. (12)) is linear in the polarizability elements, due to the coherent nature of the measurements. As a result, an inversion is performed in process 26 of FIG. 2 on the detected signal by minimizing the cost given in Eqn. (20) with respect to the polarizability $\overline{\alpha}$ using a standard single-step closed-form least squares solution. Therefore, the cost at a given k is easily reduced to a nonlinear function of $r^{(p)}$, where each value of $r^{(p)}$ has an optimal polarizability associated with it. This three-dimensional non-linear cost function can be minimized by standard optimization algorithms such as the Nelder-Mead simplex method, provided in Press et al., *Numerical Recipes* 3rd Edition: *The Art of Scientific Computing* (Cambridge U. Press, 2007), which is incorporated herein by reference. This algorithm is used in the simulations presented below. In the Nelder-Mead method a simplex, in this case defined by four points in three-dimensional space, defines a volume in search space. The cost is evaluated at each of these points and the points iterated until a local minimum is contained within a small simplex volume. The initial simplex should be made large enough to include all reasonable nanoparticle positions. The approximation of Eqn. (17) makes the evaluation of the cost inexpensive and the Nelder-Mead algorithm fast. Once a minimizing value for $r^{(p)}$ has been found, the corresponding minimizing polarizability (used in the evaluation of the cost at $r^{(p)}$) completes the estimation in process 28 of FIG. 2 of the nanoparticle parameters.

The inversion procedure described above is for a fixed value of k. To calculate the wavelength dependence of the polarizability the inversion can be performed over the full range of the wavenumber. However, the position of the nanoparticle does not vary with k and so the optimal position found at the first inversion calculation is valid over all k. Consequently, once the inversion is performed for one value of k, the position $r^{(p)}$ is known and the polarizability $\overline{\alpha}(k)$ can be found for all other values of k by a standard least-squares minimization of Eqn. (20) with $r^{(p)}$ fixed. The iterative inversion need only be performed once.

While the instrument shown in FIG. 1 can be regarded as an imaging system collecting data over spatial and spectral axes, the determination of the nanoparticle parameters is not traditional imaging. A meaningful two- or three-dimensional function is not the objective, rather a tensor and a vector are estimated from the data. The a-priori knowledge that the object can be characterized by these parameters results in a dimensionally over-constrained problem. The elements of the polarizability are coefficients of the system PSFs, which essentially act as basis functions in an alternative representation of the polarizability. The conditioning of the projection onto this basis determines the expected performance of the characterization system, with dissimilar PSFs giving better conditioning and a more accurate estimate.

Simulations

Numerical simulations now demonstrate the performance of an embodiment of the system described in the present invention. Eqns. (9) and (10), may be used to generate synthetic data. Complex white Gaussian noise is added to these data and the parameters of the nanoparticle estimated according to the method described above. By comparing the parameter estimates to those used to generate the data, the performance can be quantified. The simulations presented are at a single wavenumber as the system is not coupled across k.

To calculate synthetic data the focused field g must be found. The inversion procedure is defined in the Fourier domain and depends directly on the exit pupil fields $E^{(l)}$ shown in FIG. 4. To avoid an artificial match between the forward model and the inverse processing, it is not desirable to calculate g using numerical methods that start with $E^{(l)}$. Instead the focal field is preferably calculated using the approach outlined in Abouraddy et al., *Three-dimensional polarization control in microscopy*, Phys. Rev. Lett. 96, p. 153,901 (2006), incorporated herein by reference, where $E^{(l)}$ is decomposed into a series expansion with each term being analytically propagated into the sample. The resulting calculation involves the evaluation of one-dimensional integrals as in Richards (1959), but with higher order Bessel functions included in the integrands. This method was used to calculate the fields shown in FIG. 5.

Nanoparticle parameters to be used in the simulations are generated randomly. A polarizability is constructed by first using manipulations of a random number generator to give a random complex orthonormal spatial basis $u^{(j)}$, where j=1, 2, 3. Three unit-variance, zero-mean complex scalars $c^{(j)}$ are generated and the polarizability is then $$\overline{\alpha} = [u^{(j)}]^T c^{(j)} u^{(j)}. \quad (21)$$

This method of constructing $\overline{\alpha}$ guarantees a symmetric polarizability as physically required. A typical example of a random polarizability is $$\overline{\alpha} = \begin{bmatrix} .433 + .633i & .137 - .380i & -.308 + .424i \\ .137 - .380i & -.540 + .164i & -.096 - .293i \\ -.308 - .424i & -.096 - .293i & -.087 + .185i \end{bmatrix}, \quad (22)$$

where $\overline{\alpha}$ is represented as a matrix operating on vectors in (x,y,z) space.

The location of the nanoparticle may also be randomly generated. The values $x^{(p)}$ and $y^{(p)}$ are both normally distributed about 0 with a standard deviation of $\lambda$. The axial offset $z^{(p)}$ has a standard deviation of $\lambda/5$ and in different simulations will be given various means in order to examine how the approximation of Eqn. (17) affects performance as a function of expected defocus. An example position for the case where $\langle z^{(p)} \rangle = 0$ (where $\langle \cdot \rangle$ indicates an expected value) is, $$r^{(p)} = \lambda [-1.67 \quad -1.24 \quad -.088]^T. \quad (23)$$

Figure 9:
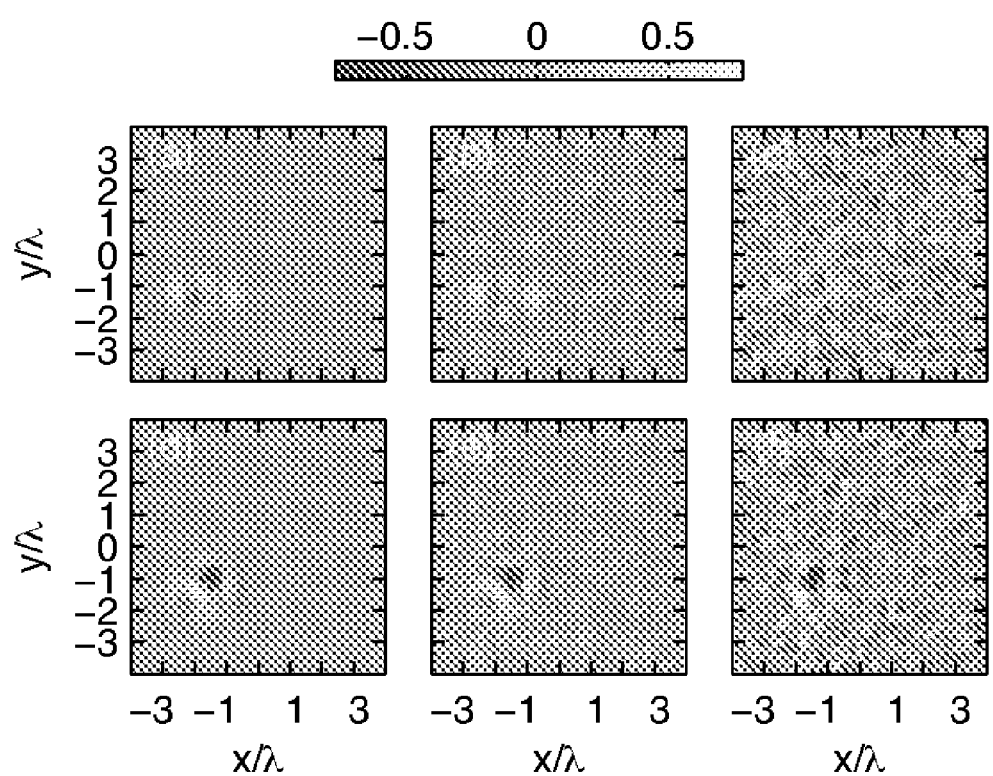
FIG. 9 depicts simulated data for the example nanoparticle parameters of Eqns. (22) and (23). The real (a-c) and imaginary (d-f) parts of the data are plotted with no noise (a,d), and SNRs of 14.3 dB (b,e) and 5.3 dB (c,f).

Complex white Gaussian noise was added to the data and the signal to noise ratio (SNR) is defined as the ratio of the noise variance and the expected square magnitude of the data from a random scatterer placed at the geometrical focus. Synthetic data at various SNRs are shown in FIG. 9 for a nanoparticle with parameters given by Eqns. (22) and (23). The focus is scanned in steps of $\lambda/4$ in both the x and y directions.

The nanoparticle position and polarizability are estimated according to the procedure described above, with the approximate model used for PSF calculation. As mentioned above, the absolute magnitude and phase of the polarizability are not easily measurable. Consequently the estimated polarization is scaled by a constant to give a minimum difference with actual polarization when making comparisons between the two. The 14.3 dB-SNR data produced from the example nanoparticle parameters was inverted to give parameter estimates of $$\hat{\alpha} = \begin{bmatrix} .417 + .622i & .137 - .401i & -.339 - .405i \\ .137 - .401i & -.543 + .170i & -.031 - .279i \\ -.339 - .405i & -.031 - .279i & -.111 + .168i \end{bmatrix}. \quad (24)$$

and $$\hat{r} = \lambda [-1.66 \quad -1.25 \quad -.085]^T. \quad (25)$$

It can be seen that these estimates show good fidelity to the original parameters.

The Nelder-Mead algorithm was implemented using the fminsearch function in the MATLAB 7.4 (Mathworks, Natick Mass.) software package. This function requires an initialization point, which was found by normalizing the Fourier-domain data $\tilde{S}$ to unit magnitude, taking the inverse Fourier transform and setting the initial value of $(x^{(p)}, y^{(p)})$ to the lateral position of the maximum-magnitude pixel. This approach is based on the phase correlation image registration technique of De-Castro et al., *Registration of translated and rotated images using finite Fourier transforms*, IEEE Trans. Pattern Analysis and Machine Intelligence PAMI-9, pp. 700-705 (1987). The initial value of $z^{(p)}$ was set to zero.

Figure 10:
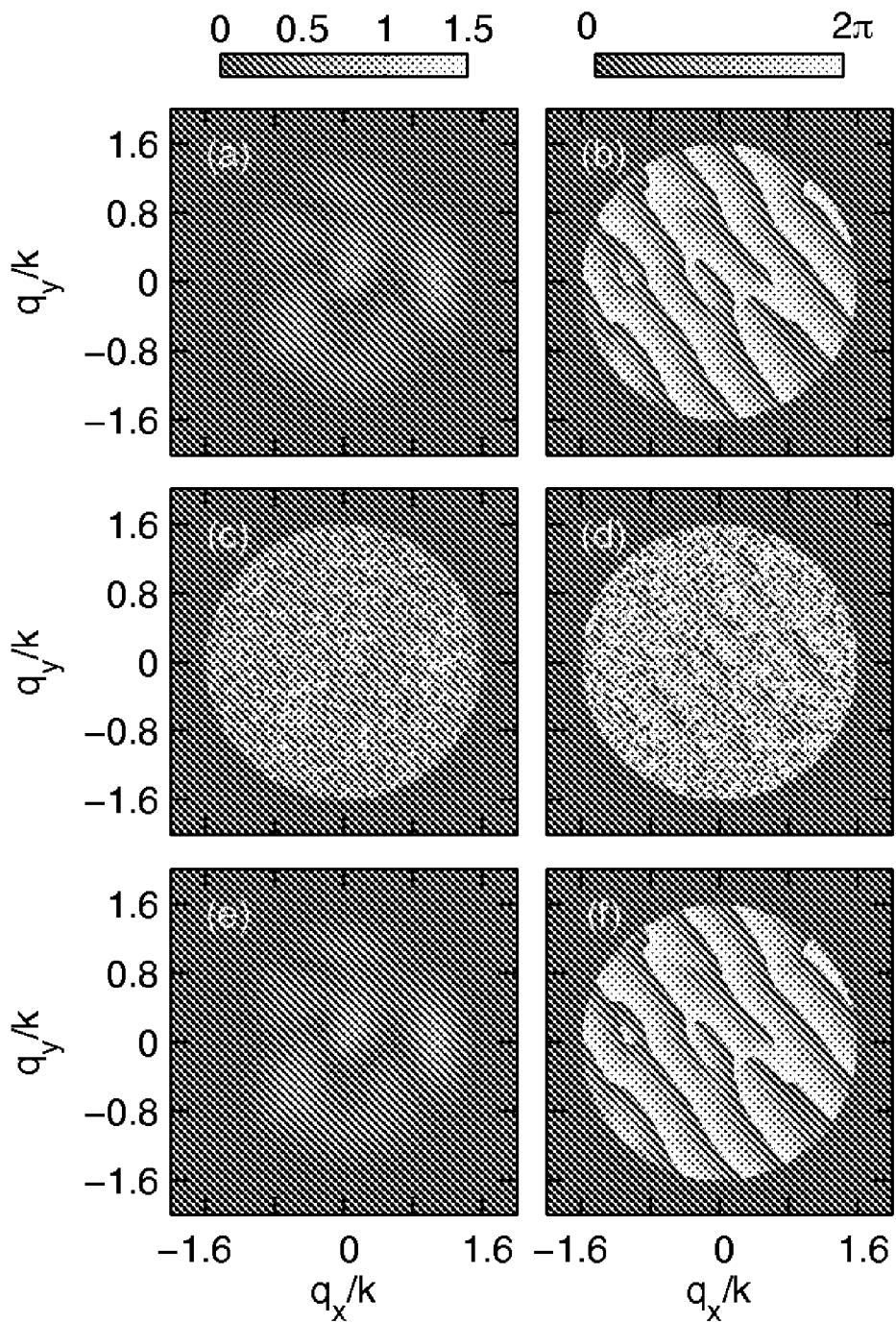
FIG. 10 depicts Fourier-domain magnitudes (a,c,e) and phases (b,d,f) of simulated data. Noise-free (a,b) and 14.3 dB-SNR (c,d) data from the example nanoparticle parameters of Eqns. (22) and (23) are shown, along with data corresponding to the estimated parameters of Eqns. (24) and (25) (e,f). Note that noise outside the system bandlimit (q=1.6) is not shown and that approximately 0.25% of the pixels in plot (c) saturate the scale.

The action of the estimation processing can also be examined in the Fourier domain. In FIG. 10, the Fourier domain data can be seen (both noise-free and at the 14.3 dB SNR noise level), along with the data corresponding to the estimated parameters. The similarity between the actual data and the estimated data indicates a small value of the cost function (Eqn. (20)). The plots seen in FIG. 10 are of high resolution, corresponding to a relatively large spatial data collection area of $30\lambda \times 30\lambda$. This range was chosen for display purposes—a smaller range can be used provided that all significant signal is collected.

The numerical experiment described above was repeated at different noise levels and different values of expected defocus $\langle z^{(p)} \rangle$, giving the results seen in FIG. 10. The quality of each polarizability and position estimate was assigned a quantitative metric: for the position estimate the metric is the $\ell^2$norm of the position error; and for the polarizability the metric is the $\ell^2$norm of the polarizability error (arranged as a 9×1) divided by the $\ell^2$norm of the polarizability. For the example random polarizability of Eqn. (22) and its estimate (Eqn. (24)), this error metric is 0.0823, while for the example location (Eqn.

(23)) and location estimate (Eqn. (25)) the error metric is 0.0103λ. Note that the estimated polarizability is scaled by a constant (accounting for unknown instrument phase and amplitude) to give the minimum error, which means that the maximum realizable polarizability error metric is 1 (achieved for a scale factor of 0).

Figure 11:
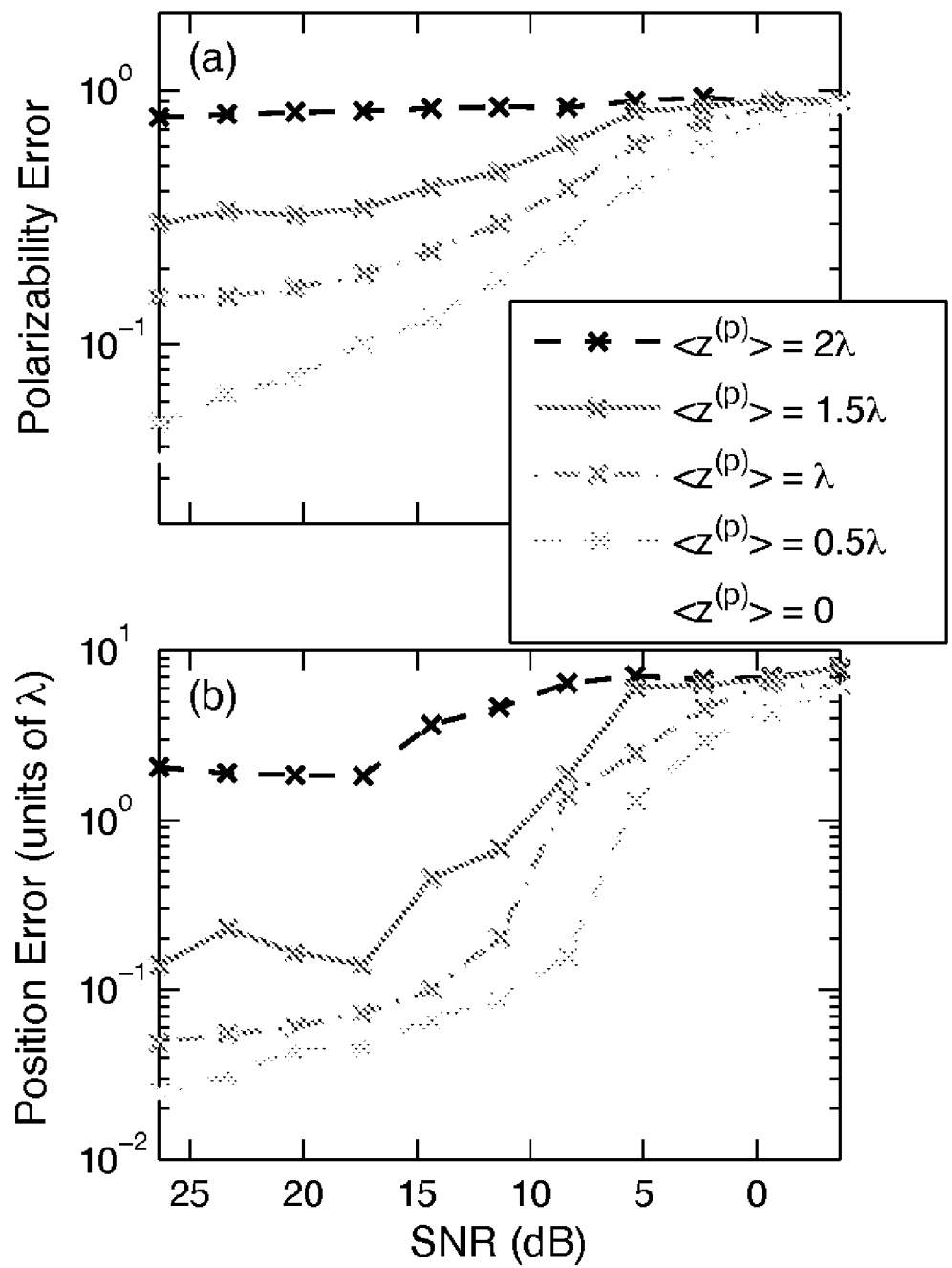
FIG. 11 shows average polarizability (a) and position (b) errors for various SNRs and expected nanoparticle distances from focus. Each marked point is calculated from 100 simulations, and each simulation has a different random nanoparticle polarizability, nanoparticle location and noise realization.

From FIG. 11 it can be seen that the reconstruction quality decreases with higher noise levels and also with the expected defocus. The degradation with $\langle z^{(p)} \rangle$ can be attributed to the Forward Model approximation breaking down. In terms of the reconstruction quality, the approximation deteriorates around ±λ of defocus and is invalid beyond ±2λ.

Summary Comments

Spectrally sensitive, two-dimensionally scanning, coherent confocal microscopes (e.g., Fourier-domain OCT instruments) may be used advantageously, as shown above, to estimate the linear polarizability of a nanoparticle as a function of wavelength. The polarizability fully determines the elastic scattering properties of the nanoparticle, provided that the particle is small enough to be characterized by a point polarizability. By measuring the polarizability, information regarding particle shape, size and orientation is obtained, suggesting applications in nanoparticle discrimination and characterization.

The main instrument modification over, for example, a high-NA Fourier-domain OCT system, is the inclusion of a vector beam shaper. The beam shaper analyzed here is piecewise constant over the lens aperture and has a binary transmittance profile, leading to a simple potential realization with half-wave plates and aperture stops. There is also considerable flexibility in modifying this beam shaper, as all that is required is the creation of diverse instrument PSFs (calculated according to Eqn. (14)) across the polarizability components.

The elements of the polarizability and the nanoparticle location are estimated from the collected data. The estimation procedure is a physically-based algorithm found by numerically solving the system inverse problem. The computational efficiency and stability of the estimation algorithm are aided by an approximation to the forward model and the fact that coherent detection means the system responds linearly to the polarizability elements. The inversion includes an iterative search method across the three nanoparticle position parameters and numerical simulations show that the result is robust to both noise and focal plane uncertainty.

The methods described herein may be applied advantageously to more general coherent processes such as second harmonic generation (SHG), within the scope of the present invention. This would provide additional nanoparticle characterization possibilities and an alternative contrast mechanism. Additionally, the methods described herein may be applied while other physical parameters of the environment in which the nanoparticle is embedded are varied. Such physical parameters may include, for example, temperature or stress in a lattice.

The present invention may be embodied in any number of instrument modalities. In alternative embodiments, the disclosed methods for evaluating nanoparticle polarizability may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product). These and other variations and modifications are within the scope of the present invention as defined in any appended claims.

We claim:

1. A method for measuring, with respect to a nanoparticle characterized by a polarizabilty, the polarizability of the nanoparticle as a function of wavelength, the method comprising:
   a. illuminating the nanoparticle with an illuminating electromagnetic wave via a first vector beam shaper;
   b. coherently detecting light scattered by the nanoparticle and propagated through a vector analyzer to generate a detected signal, wherein the vector analyzer is a beam shaper;
   c. employing a computer system to perform an inversion of the detected signal based on a comparison of the detected signal to data predicted from a forward scattering model; and
   d. estimating nanoparticle polarizability based on the inversion.

2. A method in accordance with claim 1, further comprising a step of spectrally resolving the detected light.

3. A method in accordance with claim 1, further comprising scanning the illuminating radiation in a plane transverse to the illumination direction.

4. A method in accordance with claim 1, wherein the vector analyzer is identical to the vector beam shaper.

5. A method in accordance with claim 1, further comprising varying a physical parameter of an environment in which the nanoparticle is disposed.

6. A method in accordance with claim 1, wherein the step of estimating nanoparticle polarizability includes minimizing a cost function based on a norm relating the detected signal to an estimate.

7. A method in accordance with claim 1, wherein the beam shaper is a spatially-uniform polarization analyzer rotated between sequential measurements.

8. A computer program product for use on a computer system for calculating, with respect to a nanoparticle characterized by a polarizabilty, the polarizability of the nanoparticle as a function of wavelength, the computer program product comprising a computer usable tangible medium having computer readable program code fixed thereon, the computer readable program code including:
   a. program code for generating a forward scattering model based on forward scattering by a point source;
   b. program code for receiving a signal based on coherent detection of light scattered by the nanoparticle and propagated through a vector analyzer, wherein the vector analyzer is a beam shaper;
   c. program code for performing an inversion of the detected signal based on a comparison of the detected signal to data predicted from a forward scattering model; and
   d. program code for estimating nanoparticle polarizability based on the inversion.

* * * * *